United States Patent [19]

Shidara

[11] 4,066,683
[45] Jan. 3, 1978

[54] PROCESS FOR THE PREPARATION OF DIAMINOMALEONITRILE

[75] Inventor: Hideo Shidara, Ichinomiya, Japan

[73] Assignee: Nippon Chemicals Co., Ltd., Tokyo, Japan

[21] Appl. No.: 756,182

[22] Filed: Jan. 3, 1977

[51] Int. Cl.² .......................................... C07C 120/00
[52] U.S. Cl. ............................................. 260/465.5 R
[58] Field of Search ................................ 260/465.5 R

[56] References Cited

U.S. PATENT DOCUMENTS

| | | | |
|---|---|---|---|
| 2,499,441 | 3/1950 | Woodward | 260/465.5 R |
| 3,564,039 | 2/1971 | Webster | 260/465.5 R |
| 3,629,318 | 12/1971 | Webster | 260/465.5 R |
| 3,714,222 | 1/1973 | Hartter | 260/465.5 R |

Primary Examiner—Joseph Paul Brust
Attorney, Agent, or Firm—Gordon W. Hueschen

[57] ABSTRACT

A process for the preparation of diaminomaleonitrile in high purity comprising polymerizing hydrogen cyanide in the presence of an alkyl aluminum compound having the general formula

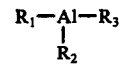

wherein $R_1$ is alkyl containing 1 to 10 carbon atoms, and $R_2$ and $R_3$ are hydrogen, halogen having 17 to 53 of atomic number or alkyl containing 1 to 10 carbon atoms.

13 Claims, No Drawings

PROCESS FOR THE PREPARATION OF DIAMINOMALEONITRILE

The present invention relates to a process for the preparation of diaminomaleonitrile and, more particularly, to an improved process for the preparation of diaminomaleonitrile by polymerizing hydrogen cyanide in the presence of alkyl aluminum and its derivatives.

Diaminomaleonitrile is known as a tetramer of hydrogen cyanide, having the structural formula:

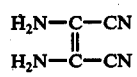

and is of great value as a starting compound for the synthesis of various heterocyclic compounds, especially as a raw material for the manufacture of intermediates and medicinal compounds, such as dicyanopyrazine, adenine and dicyanoimidazole, various chemicals, agricultural chemicals and additives for foodstuffs. However, it has been of a very high price because there has not been developed any favorable process for the synthesis thereof.

In a prior process, diaminomaleonitrile has been prepared by polymerizing hydrogen cyanide in a presence of a basic compound such as alkali cyanides, trialkylamines or organic quaternary ammonium hydroxides as a catalyst and separating and purifying diaminomaleonitrile from the resulting polymerizate. This prior process, however, is low in reaction rate and in yield.

Recently, great advance and improvement have been accomplished and more than 50% of yield can be obtained as disclosed in Japanese Patent Open No. 2917/1971 and Japanese Patent Publication No. 5925/1972. In the former process diaminomaleonitrile is prepared by polymerizing hydrogen cyanide using cyanogen together with hydrogen cyanide in a solvent in the presence of a basic compound such as trialkylamines. According to this process, although about 70% of yield can be attained, a large amount of cyanogen should be employed. Therefore, cyanogen should be previously prepared, so a special apparatus and process are necessary.

In the latter process, it is prepared by dissolving hydrogen cyanide into dissolving dimethylsulfoxide, adding sodium cyanide as a catalyst and heating it in an autoclave. However, this process has some disadvantages that separation and further recovering purification process of dimethylsulfoxide is necessary.

Further, polymerizate of hydrogen cyanide obtained by the above mentioned any known methods contains a large amount of perpolymerizate, diaminomaleonitrile has low purity, thus diaminomaleonitrile should be obtained by complicated purification processes.

Accordingly, an object of the present invention is to provide a novel process for the preparation of diaminomaleonitrile.

Another object of the present invention is to provide a process for the preparation of diaminomaleonitrile in high purity.

A still another object of the present invention is to provide a process for the preparation of highly pure diaminomaleonitrile by a simple process in high yield.

The aforesaid objects are accomplished by a process for the preparation of diaminomaleonitrile comprising polymerizing hydrogen cyanide in the presence of an alkyl aluminum compound. According to the present invention, considerably highly pure diaminomaleonitrile can be obtained in considerably high yield.

The alkyl aluminum compound used in the present invention is one having at least one alkyl group in a molecule and has the following general formula:

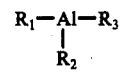

wherein $R_1$ is alkyl containing 1 to 10 carbon atoms, and $R_2$ and $R_3$ are hydrogen, halogen having 17 to 53 of atomic number or alkyl containing 1 to 10 carbon atoms.

In the above mentioned formula, $R_1$ is preferably alkyl containing 1 to 5 carbon atoms, and $R_2$ and $R_3$ are one member selected from the group consisting of hydrogen, chlorine, bromine, iodine and alkyl containing 1 to 5 carbon atoms. $R_1$, $R_2$ and $R_3$ are more preferably alkyl containing 1 to 10 carbon atoms and most preferably alkyl containing 1 to 5 carbon atoms.

Typical alkyl aluminum compounds are trimethyl aluminum, triethyl aluminum, tri-n-propyl aluminum, triisopropyl aluminum, tri-n-butyl aluminum, triisobutyl aluminum, tri-tert-butyl aluminum, tripentyl aluminum, trihexyl aluminum, triheptyl aluminum, trioctyl aluminum, trinonyl aluminum, tridecyl aluminum, dimethyl aluminum hydride, diethyl aluminum hydride, di-n-propyl aluminum hydride, diisopropyl aluminum hydride, di-n-butyl aluminum hydride, diisobutyl aluminum hydride, di-tert-butyl aluminum hydride, dimethyl aluminum chloride, diethyl aluminum chloride, di-n-propyl aluminum chloride, diisopropyl aluminum chloride, di-n-butyl aluminum chloride, diisobutyl aluminum chloride, di-tert-butyl aluminum chloride, dihexyl aluminum chloride, dioctyl aluminum chloride, dimethyl aluminum bromide, diethyl aluminum bromide, di-n-propyl aluminum bromide, diisopropyl aluminum bromide, di-n-butyl aluminum bromide, di-tert-butyl aluminum bromide, dihexyl aluminum bromide, dioctyl aluminum bromide, dimethyl aluminum iodide, diethyl aluminum iodide, di-n-propyl aluminum iodide, diisopropyl aluminum iodide, di-n-butyl aluminum iodide, diisobutyl aluminum iodide, di-tert-butyl aluminum iodide, dihexyl aluminum iodide, dioctyl aluminum iodide, methyl aluminum dichloride, ethyl aluminum dichloride, n-propyl aluminum dichloride, isopropyl aluminum dichloride, n-butyl aluminum dichloride, isobutyl aluminum dichloride, tert-butyl aluminum dichloride, hexyl aluminum dichloride, octyl aluminum dichloride, methyl aluminum dibromide, ethyl aluminum dibromide, n-propyl aluminum dibromide, isopropyl aluminum dibromide, n-butyl aluminum dibromide, isobutyl aluminum dibromide, tert-butyl aluminum dibromide, hexyl aluminum dibromide, octyl aluminum dibromide, methyl aluminum diiodide, ethyl aluminum diiodide, n-butyl aluminum diiodide, isobutyl aluminum diiodide, tertbutyl aluminum diiodide, hexyl aluminum diiodide and octyl aluminum diiodide. The alkyl aluminum compound may be used in amounts of the molar ratio to hydrogen cyanide of from 0.001 to 1, preferably from 0.005 to 0.1.

According to the present invention, although polymerization of hydrogen cyanide may be carried out in the absence of a solvent, it is preferably treated and subjected to reaction under an inert gas and/or a solvent. Any solvent which can be dissolved the alkyl aluminum compound and does not decompose it may be used. Typical solvents are an aromatic hydrocarbon such as benzene, toluene, xylene, pseudocumene, durene, etc., an aliphatic or alicyclic hydrocarbon such as hexane, heptane, octane, decane, dodecane, cyclohexane, cycloheptane, cyclododecane, etc. The solvent may be used in amounts of the weight ratio to hydrogen cyanide of generally from 1 to 50, preferably 10 to 30.

Reaction temperature in the present invention is generally −20° to + 150°C, preferably −10° to + 50° C, most preferably 0° to + 20° C. Although reaction time depends upon the amounts of the catalyst, it is generally 1 hour to 7 days, preferably 24 to 96 hours. If alkyl aluminum halide is used as a catalyst, reaction rate is increased by adding a basic compound such as trimethylamine, triethylamine, tripropylamine, tributylamine and the like in an about equivalent. Reaction pressure is automatically decided based on used amount of the catalyst, amount of the solvent and the reaction temperature, but high pressure is not necessary, and good results in yield and purity can be obtained by carrying out the reaction for a long time in a dilute solution.

When the solvent is used, reaction product is precipitated, so white needle crystals of highly pure diaminomaleonitrile can be obtained only by filtrating the precipitate by a screen or a filter after completion of reaction and drying it. Further, the catalyst is still remained in the solvent after removing the reaction product, so it can be repeatedly used in the subsequent reaction by filtrating the solvent by means of usual filter paper or cloth.

As mentioned above, condiderably highly pure diaminomaleonitrile can be obtained in high yield by employing the alkyl aluminum compound as a polymerization catalyst for hydrogen cyanide in the present invention, so purification thereof is not substantially necessary, it is very economical on account of high yield. Further, in case of solution polymerization the reaction product is precipitated during the reaction, so diaminomaleonitrile can be obtained as a highly pure white crystals merely by filtration after completing the reaction. Thus not only the separation process of the reaction product is simple, but also alkyl aluminum compound used as the catalyst can be easily removed by filter paper or cloth after completing the reaction. Therefore, there are advantages that special recovering purification process for the solvent is not necessary and it can be repeatedly used as it is for the subsequent reaction.

The present invention will be more illustrated by the following Examples. All of yields of diaminomaleonitrile in the following Examples are percent by weight.

EXAMPLE 1

In a round-bottomed flask of a capacity of 200 ml having a stopper, there was charged 140 ml of toluene, then added thereto 2 ml of triethyl aluminum and 5.0 g of hydrogen cyanide. The flask was then put in a thermostat and maintained at 5° C. After 72 hours, the reaction mixture was filtered by a screen (80 meshes) to obtain 4.8 g of white needle crystals of diaminomaleonitrile (yield 96.0%). This diaminomaleonitrile was subjected to purity analysis. That is to say, a spot of diaminomaleonitrile was separated by a thin layer chromatography, and it was desorbed by water, and then it was analysed by an ultraviolet spectrophotometer using a wave length of 295 mγ. Purity of diaminomaleonitrile thus obtained was 98.0%.

EXAMPLE 2

In a round-bottomed flask of a capacity of 200 ml having a stopper, there was charged 120 ml of xylene, then added thereto 2 ml of tri-n-propyl aluminum and 5.0 g of hydrogen cyanide. The flask was then put in a thermostat and maintained at 10° C. After 48 hours, the reaction mixture was filtered by a screen (80 meshes) to obtain 3.6 g of white needle crystals of diaminomaleonitrile (yield 74.0%). This diaminomaleonitrile was subjected to purity analysis by a similar method as in Example 1 to obtain 97.3% of purity.

EXAMPLE 3

In a round-bottomed flask of a capacity of 200 ml having a stopper, there was charged 140 ml of toluene, then added thereto 2 ml of triisobutyl aluminum and 5.0 g of hydrogen cyanide. The flask was then put in a thermostat and maintained at 5° C. After 72 hours, the reaction mixture was filtered by a screen (80 meshes) to obtain 3.2 g of white needle crystals of diaminomaleonitrile (yield 64.0%). This diaminomaleonitrile was subjected to purity analysis by a similar method as in Example 1 to obtain 97.5% of purity.

EXAMPLE 4

In a round-bottomed flask of a capacity of 200 ml having a stopper, there was charged 140 ml of toluene, then added thereto 2 ml of diethyl aluminum chloride, 2.3 ml of triethylamine and 5.0 g of hydrogen cyanide. The flask was then put in a thermostat and maintained at 5° C. After 72 hours, the reaction mixture was filtered by a screen (80 meshes) to obtain 3.0 g of white needle crystals of diaminomaleonitrile (yield 60.0%). This diaminomaleonitrile was subjected to purity analysis by a similar method as in Example 1 to obtain 91.3% of purity.

EXAMPLE 5

In a method of Example 1, tolune after removing diaminomaleonitrile was filtered by a filter paper to remove the catalyst. Then 2 ml of triethyl aluminum and 5.0 g of hydrogen cyanide were charged into it and maintained at 5° C. After 72 hours, the reaction mixture was filtered by a screen (80 meshes) to obtain 4.8 g of white needle crystals of diaminomaleonitrile. This diamonomaleonitrile was subjected to purity analysis by a similar method as in Example 1 to obtain 96.2% purity.

What is claimed is:

1. A process for the preparation of diaminoaleonitrile comprising polymerizing hydrogen cyanide in the presence of an alkyl aluminum compound having the general formula

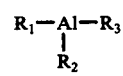

wherein $R_1$ is alkyl containing 1 to 10 carbon atoms, and $R_2$ and $R_3$ are hydrogen, halogen having 17 to 53 of atomic number or alkyl containing 1 to 10 carbon atoms, wherein the alkyl aluminum compound is used in amounts of the molar ratio to hydrogen cyanide of from 0.001 to 1, and wherein the reaction is carried out at a temperature of from about −20° C to about +150° C.

2. A process according to claim 1, wherein the alkyl aluminum compound is used in amounts of the molar ratio to hydrogen cyanide of from 0.005 to 0.1.

3. A process according to claim 1, wherein the reaction is carried out at a temperature of −10° to + 50° C.

4. A process according to claim 1, wherein the alkyl aluminum compound has the following general formula

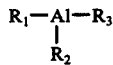

wherein $R_1$ is alkyl containing 1 to 5 carbon atoms, and $R_2$ and $R_3$ are one member selected from the group consisting of hydrogen, chlorine, bromine, iodine and alkyl containing 1 to 5 carbon atoms.

5. A process according to claim 1, wherein the alkyl aluminum compound has the following general formula

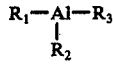

wherein $R_1$ is alkyl contanning 1 to 5 carbon atoms, and $R_2$ and $R_3$ are one member selected from the group consisting of chlorine, bromine and alkyl containing 1 to 5 carbon atoms.

6. A process according to claim 1, wherein the alkyl aluminum compound is a trialkyl aluminum having general formula

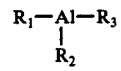

wherein $R_1$, $R_2$ and $R_3$ are alkyl containing 1 to 10 carbon atoms.

7. A process according to claim 1, wherein the alkyl aluminum compound is a trialkyl aluminum having general formula

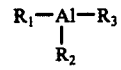

wherein $R_1$, $R_2$ and $R_3$ are alkyl containing 1 to 5 carbon atoms.

8. A process according to claim 1, wherein the reaction is carried out in a solvent.

9. A process according to claim 8, wherein the solvent is at least one member selected from the group consisting of aromatic, aliphatic and alicyclic hydrocarbons.

10. A process according to claim 8, wherein the solvent is aromatic hydrocarbons.

11. A process according to claim 7, wherein the trialkyl aluminum is triethyl aluminum.

12. A process according to claim 7, wherein the trialkyl aluminum is tri-n-propyl aluminum.

13. A process according to claim 7, wherein the trialkyl aluminum is triisobutyl aluminum.

* * * * *